United States Patent
Suzuki et al.

[11] Patent Number: 5,155,259
[45] Date of Patent: Oct. 13, 1992

[54] ALDOSE REDUCTASE INHIBITOR

[75] Inventors: Yukio Suzuki; Kouichi Kuno; Motoshi Shoda; Masao Yaso; Satoshi Yaginuma; Akira Asahi, all of Shizuoka, Japan

[73] Assignee: Toyo Jozo Kabushiki Kaisha, Shizuoka, Japan

[21] Appl. No.: 742,352

[22] Filed: Aug. 8, 1991

[30] Foreign Application Priority Data

Aug. 8, 1990 [JP] Japan .................. 2-208128

[51] Int. Cl.⁵ .................. C07C 59/40; A01N 37/10
[52] U.S. Cl. .................. 562/469
[58] Field of Search .................. 562/469; 514/570

[56] References Cited
PUBLICATIONS

Node, M. et al., J. Org. Chem. 46(10) 1991-3, 1981.
Luedemann, H., Macromol. Chem. 175(8) 2393-407, 1974.
Pachaly, Peter, Arch. Pharm. 322(8) 483-7, 1989.
Chaudhury, H. et al., J. Chem. Soc. C16, 2070-7, 1969.

*Primary Examiner*—Paul J. Killos
*Attorney, Agent, or Firm*—Young & Thompson

[57] ABSTRACT

An aldose reductase inhibitor, comprising a compound of the formula (I)

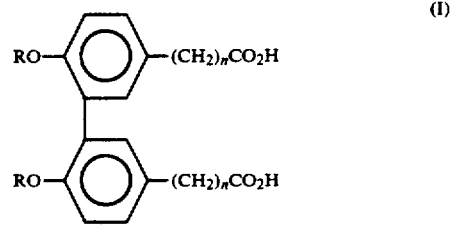

or a pharmaceutically acceptable salt thereof as the effective component, in which R is lower alkyl or cyclohexylmethyl and n is 2 or 3. The compounds of formula (I) and salts thereof according to the invention exhibit a superior aldose reductase inhibiting activity with simultaneous high stability, so that they are useful for the prevention and therapy of diabetic complications.

4 Claims, No Drawings

ALDOSE REDUCTASE INHIBITOR

FIELD OF THE INVENTION

This invention relates to an aldose reductase inhibitor.

BACKGROUND OF THE INVENTION

Among biphenyl derivatives having an inhibiting activity for aldose reductase, there have been known aldostatin (as disclosed in Japanese patent application Kokai No. 205095/1987) and FR 900280 (as disclosed in Japanese patent application Kokai No. 72144/1990), which are now under examination for their application to the prevention of therapy of diabetic complications, such as cataracts, retinal disease, neuropathy, nephropathy and so on.

Nevertheless, there is still a need to develop substances having a higher aldose reductase inhibiting activity than those of the prior art.

The inventors have studied the pharmacodynamics of various compounds to find new aldose reductase inhibitors exhibiting superior inhibiting activity and have discovered that a series of new biphenyl derivatives of the formula (I)

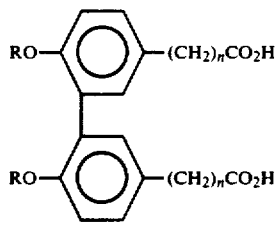

in which R denotes lower alkyl or cyclohexylmethyl and e,uns/n/ is 2 or 3, have greater activity for inhibiting aldose reductase than those known heretofore.

SUMMARY OF THE INVENTION

Thus, the present invention provides new aldose reductase inhibitors containing, as the effective component, a compound or a pharmaceutically acceptable salt thereof represented by the formula (I)

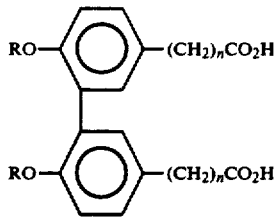

in which R and e,uns/n/ have the meanings given above.

Among the compounds of formula (I), especially those in which R denotes an alkyl group having 1-5 carbon atoms or a cyclohexylmethyl group are preferred.

Of these compounds of formula (I), the compound in which R denotes methyl and e,uns/n/ is 3 is known (Indian Chem. Soc. 42, 86 (1965)), but its pharmacological utility has not yet been reported. All the others are novel compounds. While these novel compounds can be produced by a production process similar to that of the known compound mentioned above, it is also possible to synthesize them pursuant to the reaction scheme given below.

Thus, they are produced in accordance with the following reaction scheme:

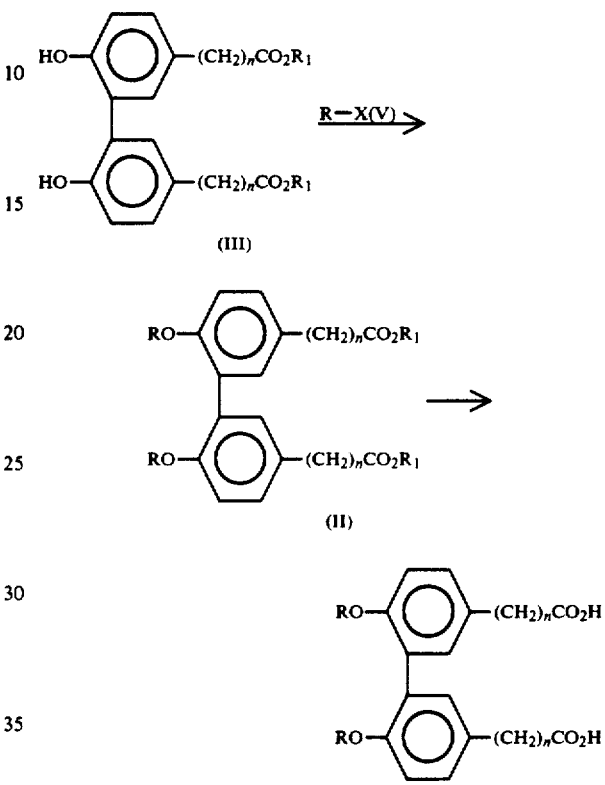

in which R and $\underline{n}$ have the meanings as given above, $R_1$ represents a radical removable by hydrolysis and X denotes a halogen atom, by alkylating the phenolic hydroxyl groups of an esterified biphenyl dicarboxylic compound of formula (III) using an alkyl halide of formula (V) into the compound of formula (II) and then splitting the ester group of formula (II) into a free acid of formula (I).

DETAILED DESCRIPTION OF THE INVENTION

As the alkyl halide of formula (V) used for alkylating the esterified compound of formula (III), there may be exemplified alkyl iodides and alkyl bromides of 1-5 carbon atoms, cyclohexylmethyl bromide and so on.

The alkylation can be performed in an organic solvent which will not participate in the reaction, such as DMF, acetone, dioxane, tetrahydrofuran, benzene, toluene, xylene, ethyl acetate, methanol, ethanol or so on, by introducing therein the esterified compound (III) and the alkyl halide (V) and conducting the reaction in the presence of an inorganic or organic base, for example, an alkali metal carbonate such as anhydrous potassium carbonate or anhydrous sodium carbonate; an alkali metal hydroxide such as sodium or potassium hydroxide; a tertiary alkylamine such as trimethylamine or triethylamine; pyridine, or a pyridine derivative such as picoline, lutidine or 4-dimethylaminopyridine; a diazabicyclo compound such as 1,5-diazabicyclo (4.3.0)-nonene-5, 1,4-diazabicyclo (2.2.2)-octane, 1,8-diazabicyclo (5.4.0)-undecene-7; or a metal alkoxide such as sodium methoxide or sodium ethoxide, together with, if necessary, a small amount of copper powder as catalyst.

The reaction is carried out in general at room temperature, or under heating to 60°-100° C. for poorly reactive compounds, for 2-6 days with stirring. The amount of the reagents and catalyst may preferably be in the range from 5 to 40 moles of the halide, from 2 to 7 of the base and from 0.5 to 1.5 times by weight of the catalyst per mole of the starting compound.

Among the starting compounds, namely, the esterified biphenyl compounds of formula (III), the compound in which n is 2 is known ((J. Org. Chem. 46. 1991 (1981)) and the compound in which e,uns/n/ is 3 (IIIb) can be prepared easily as shown in the following reaction scheme:

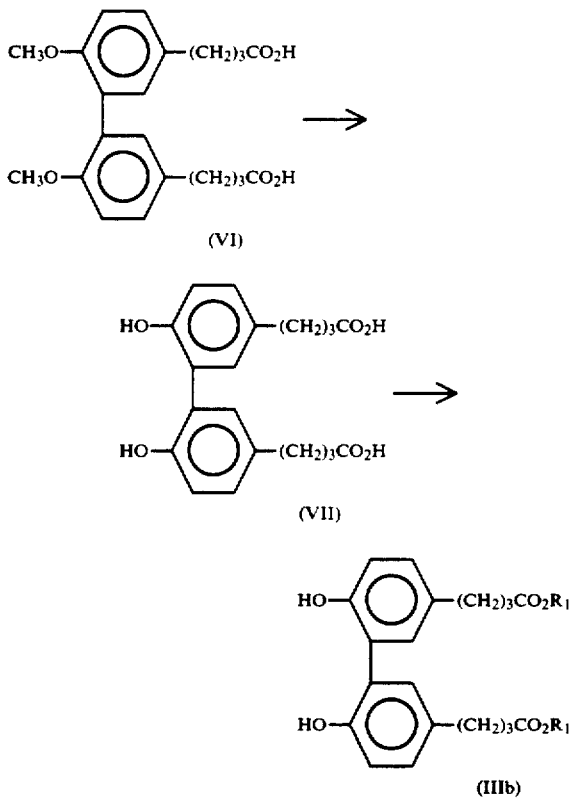

by reacting pyridine-hydrochloric acid with a known compound of formula (VI) at about 180° C. to convert the methoxy group into hydroxide, and then esterifying the carboxyl groups of the resulting product of formula (VII) with a lower alcohol or the like.

The ester splitting, namely, hydrolysis of the ester groups of the resulting compound of formula (II), can be effected by reacting the ester in an organic solvent such as ethanol, methanol, dioxane, tetrahydrofuran or acetonitrile, with a base such as sodium hydroxide or potassium hydroxide for 1-4 days at room temperature with stirring. The concentration of the base to be employed may in general be in the range from 1 to 3 N and it is preferably to use it in an amount of about 8 moles per mole of the compound of formula (II).

A compound of formula (I) according to the present invention obtained as above can further be purified as required using any known purifying means such as column chromatography on silica gel, recrystallization and so on.

A compound of formula (I) according to the present invention can be converted into a corresponding pharmaceutically acceptable salt of an inorganic cation of, for example, an alkali metal such as sodium or potassium; an alkaline earth metal such as calcium or magnesium; and ammonium, or an organic cation of, for example, a non-toxic organic amine.

For preparing an inorganic salt, the compound of formula (I) according to the present invention is preferably dissolved first in an aqueous solution containing at least an equivalent amount of hydroxide, carbonate or of a metal corresponding to the contemplated inorganic salt. For such salt formation by reaction with a metal compound, a water-miscible organic solvent inert to the reaction, such as methanol, ethanol, acetone or dioxane may be admixed with the reaction mixture. If sodium hydroxide, sodium carbonate or sodium bicarbonate is employed, a solution of the corresponding sodium salt will be obtained.

A solid salt can be obtained by evaporating off the solvent of such solution or by adding to the solution a water-soluble organic solvent having some polarity, such as butanol, ethyl methyl ketone or so on, to cause deposition of the solid salt.

The compounds of formula (I) according to the present invention or the pharmaceutically acceptable salts thereof can be administered to humans as an aldose reductase inhibitor as such or in the form of a preparation with a known carrier substance.

The aldose reductase inhibitor according to the present invention can be administered to human patients or to experimental animals, for example, orally, rectally or parenterally, such as, by intravenous, intramuscular, subcutaneous and intraperitoneal administration and by eye wash. The preparation of the compound according to the present invention may be formulated so as to adapt to each of the above administration techniques.

The preparation may be in any conventional form for human administration, such as pellets, pills, powders, granules, capsules, suppositories, injectables, eye drops and eye wash. For formulating such preparations for oral administration, such as tablets, granules and capsules, the compound according to the present invention may be mixed with, for example, an excipient serving as a carrier substance, such as starch, lactose, sucrose, mannite, carboxymethyl cellulose, corn starch and various inorganic salts; binders such as starch, dextrin, gum arabic, gelatin, hydroxypropyl starch, methyl cellulose, sodium carboxymethyl cellulose, hydroxypropyl cellulose, crystalline cellulose, ethyl cellulose, polyvinyl pyrrolidone and macrogol; disintegrators such as starch, hydroxypropyl starch, carboxymethyl cellulose, sodium carboxymethyl cellulose and hydroxypropyl cellulose; surface active agents, such as sodium lauryl sulfate, soybean lecithin, fatty acid esters of sucrose and polysorbate 80; lubricating agents, such as talc, wax, hydrogenated vegetable oil, fatty acid esters of sucrose, magnesium stearate and calcium stearate; fluidizing agents; coloring agents and flavors and so on.

The compounds of formula (I) according to the present invention or pharmaceutically acceptable salts thereof can be administered in the form of suspensions, emulsions, syrups or elixirs.

For parenteral preparations, there may be used distilled water for use for injection, physiological saline solutions, aqueous solutions of glucose, vegetable oils for injection, propylene glycol, polyethylene glycol and so on as the diluent. It is permissible to further incorporate as required sterilizers, antiseptics, stabilizers and so on. It is possible to prepare such parenteral preparations, in consideration of their low stability as freeze-dried products by subjecting the preparation placed in a suitable vessel, such as a glass vial, to freeze drying, so as to permit reproducing the preparation directly before its use by diluting with an appropriate diluent. It is also possible to incorporate into the preparation as required isotonating agents, stabilizers, aseptics, analgesics and so on.

The administration rate of the compound of formula (I) or the pharmaceutically acceptable salt thereof according to the present invention may vary in accordance with each selected administration course and with the condition of the acceptor to be administered, such as age, body weight, disease condition and so on. It may be in general in the range from 5 milligrams to 1 gram, preferably in the range from about 25 milligrams to 1 gram, preferably in the range from about 25 milligrams to about 300 milligrams, calculated as the compound of formula (I), as the total amount per day for an adult human, by administration once a day or in two or three daily aliquots.

Various compounds of formula (I) according to the present invention have been examined for their pharmacodynamic behavior and for their acute toxicity, of which the results are given below.

METHOD FOR DETERMINING THE ENZYME REACTION INHIBITING ACTIVITY

The preparation of aldose reductase and the determination of its enzyme reaction inhibiting activity were carried out pursuant to the procedures disclosed by Haymann et al. in *Journal of Biological Chemistry*, 240, 877 (1965).

The sample solution to be examined for inhibiting activity was prepared by dissolving an amount of a compound of formula (I) according to the present invention in a small amount of methanol and increasing the volume of the resulting methanol solution by diluting it with distilled water up to tenfold volume. As the enzyme, i.e. aldose reductase, originating from the lens of cattle, was employed after being subjected to a partial purification.

To 2.4 ml of $5 \times 10^{-5}$ M NADPH solution dissolved in a 2/15 M phosphate buffer solution (pH 6.0), 0.4 ml of the enzyme solution and 0.1 ml of the sample solution to be examined were added and the mixture was charged in a quartz cell in a photoelectric photometer and was subjected to preincubation at 37° C. for 4 mins. Then, 0.1 ml of a 0.015 M D,L-glyceraldehyde solution was added thereto for initiating the enzyme reaction and the decrease in the photoabsorbance at 340 nm was measured at 37° C. for 4 mins. The aldose reductase inhibiting activity calculated by $$\frac{B - A}{B} \times 100\ (\%)$$

in which A represents the enzyme reaction rate with addition of the inhibitor and B denotes the enzyme reaction rate without addition of the inhibitor.

2) ACTIVITY FOR SUPPRESSING ACCUMULATION OF SORBITOL

(A) Tissue Culture

Lenses and sciatic nerves excised from 7 weeks-old male Wistar rats were washed twice with an aseptic buffer solution consisting of 0.3% trisaminomethane, 0.8% NaCl, 0.038% KCl, 0.025% $Na_2HPO_4.12H_2O$, 0.1% glucose and 1.85 ml/l of concentrated HCl.

The lenses and the sciatic nerves were then treated by a 30 mins. preculture in a culture medium prepared by adding 2 ml of 7.5% conc. aseptic $NaHCO_3$ solution and 5.5 ml of aseptic calf fetus serum to 100 ml of an aseptic culture medium of 0.98% TC Medium 199 (supplied from the firm NISSUI) containing 0.01% of dihydro-streptomycin and 0.01% of benzyl-penicillin. Thereafter, the intrinsic culture was effected in a culture medium prepared by adding each sample solution to be examined and 0.09% of glucose to the above-mentioned culture medium and permitting culturing to proceed for 20 hours. The culturing was effected at 37° C. in an atmosphere composed of 95% air and 5% $CO_2$.

After culturing, the cultured samples of lens and sciatic nerve were removed from the culture medium to filter paper and the weight of each of them was measured after the adherent culture solution had been blown off. Then, each of the cultured samples was homogenized with the addition of 1 ml of a cold 8% $HClO_4$ solution and the homogenized mixture was subjected to centrifugation at 10,000 G for 10 mins., whereby a supernatant was obtained. The resulting precipitate was then homogenized again with addition thereto of 0.5 ml of cold 8% $HClO_4$ solution and the homogenized mixture was again subjected to centrifugation in a similar way as above to obtain a further supernatant. This was combined with the previously obtained supernatant and the resulting solution was neutralized with 2 N KOH aq. solution and was diluted with distilled water to a volume of 5 ml. The precipitate formed by neutralization was separated by centrifugation at 3,000 rpm for 10 mins. and the resulting supernatant was employed as the sample for determining the sorbitol content.

(B) Determination of Sorbitol Content

The determination of the sorbitol content in the lens and in the sciatic nerve was carried out in accordance with the technique of Bergmeyer in "*Methods of Enzymatic Analysis*" edited by H.U. Bergmeyer, pp 1323-1326, Academic Press, New York, 1974 and in accordance with the technique proposed by Malaon et al. in "*Diabetes*" 29, 861-864 (1980).

To 0.5 ml of the sample solution for determination of sorbitol content obtained as above, 0.9 ml of 0.1 M glycine-KOH buffer solution (pH 9.4) containing 1 mM of $NAD^+$ and 0.1 ml of a solution of sorbitol dehydrogenase of 20 units/ml were added and the resulting mixture was subjected to incubation at 37° C. for 1 hour.

The content of sorbitol in each tissue was estimated by assuming the increment of the photoabsorbance at 340 nm to be proportional to the amount of NADH produced by the reaction for the lens and by detecting the fluorescence with an excitation wavelength of 366 nm and a fluorescence wavelength of 425 nm for the sciatic nerve.

The activity for suppressing accumulation of sorbitol, i.e. the aldose reductase inhibiting activity, was calculated from the determined sorbitol content by the calculation formula $$\frac{(B - C) - (A - C)}{(B - C)} \times 100\ (\%)$$

in which A denotes the content of sorbitol per unit weight of the tissue after cultivation with addition of the inhibitor, B denotes the sorbitol content per unit weight of the tissue after cultivation without addition of the inhibitor and C represents the sorbitol content per unit weight of the tissue after cultivation in the medium without addition of glucose and inhibitor.

The results of the tests according to 1) and 2) above are summarized in Table 1 below. Here, it is to be pointed out that the diester intermediate of formula (II) in the production of the compound of formula (I) according to the present invention and the products obtained in Reference Examples 1-8 hereinafter as well as the compound 2,2'-dimethoxy-5, 5'-bis(3-carboxypropyl) biphenyl diester, in themselves did not exhibit any aldose reductase inhibiting activity, i.e. exhibited no activity for suppressing accumulation of sorbitol.

TABLE 1

(I')

RO—⟨○⟩—(CH$_2$)$_n$CO$_2$H

RO—⟨○⟩—(CH$_2$)$_n$CO$_2$H

| Compound of formula(I') R | n | Enzyme Reaction Inhibiting Activity (%)[1] | Inhibition of Sorbite Accumulat. in Lens (%)[2] | Inhibition of Sorbite Accum. in Sciatic N. (%)[3] |
|---|---|---|---|---|
| CH$_3$— | 2 | 44 | 76 | 85 |
| C$_2$H$_5$— | 2 | 43 | 56 | 69 |
| C$_3$H$_7$— | 2 | 35 | 66 | 67 |
| ⟨○⟩—CH$_2$— | 2 | 44 | 51 | — |
| CH$_3$— | 3 | 63 | 85 | 92 |
| C$_2$H$_5$— | 3 | 77 | 76 | 80 |
| C$_3$H$_7$— | 3 | 57 | 68 | 67 |
| ⟨○⟩—CH$_2$— | 3 | 45 | 57 | — |
| C$_5$H$_{11}$— | 3 | 48 | — | — |

Notes:
[1]Tests were carried out at a concentration of 0.1 γ.
[2]Tests were carried out at a concentration of 2.5 γ.
[3]Tests were carried out at a concentration of 1.0 γ.

3) ACUTE TOXICITY

Compounds of formula (I) according to the present invention, as given in the examples below or 2,2'-dimethoxy-5, 5'-bis(3-carboxypropyl) biphenyl, were suspended in distilled water and were dissolved completely by adding at least the equimolar amount of aqueous NaOH solution. The pH of the resulting solutions was adjusted to 6.5-7.0 and the solutions were administered to groups of 5 weeks old STD-DDY mice (each group consists of 3 mice) orally at a rate of 400 mg/20 ml/kg and each group was observed for 10 days. No fatality was marked in any of the administered groups.

As is clear from the experimental results, the compounds according to the present invention exhibit a superior aldose reductase inhibiting activity and excellent stability, so that they can be used advantageously as aldose reductase inhibitors for the prevention or therapy of cataracts, retinal diseases, neuropathy, nephropathy, corneal disorders, diabetic uveitis and so on.

PREFERRED EMBODIMENTS OF THE INVENTION

Below, the present invention will further be described in more detail by way of concrete Examples and several Reference Examples.

REFERENCE EXAMPLE 1

Synthesis of 2,2'-dimethoxy-5,5'-bis(2-ethoxycarbonylethyl) biphenyl

To 5 ml of a DMF solution containing 200 mg (0.05181 mmol) of 2,2'-dihydroxy-5,5'-bis(2-ethoxycarbonylethyl) biphenyl and 2.316 ml (20.72 mmol) of methyl iodide, there was added 572 mg (2.072 mmol) of anhydrous potassium carbonate and a small amount of copper powder and the resulting mixture was agitated for 4 days at room temperature and for a further 2 days at 60° C. The reaction mixture was filtered by suction through Celite to remove the solid matter, which was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and saline solution in this sequence and was dried over anhydrous sodium sulfate. The residue obtained after the solvent had been evaporated off was purified by silica gel column chromatography (with 20 g of WAKO-gel C-200, eluent: toluene and toluene/ethyl acetate of 50/1) to obtain 182 mg (0.4936 mmol, 85%) of 2,2'-dimethoxy-5,5'-bis(2-ethoxycarbonylethyl) biphenyl as an oily product.

$^1$H-NMR (CDCl$_3$),

δ(ppm): 1.24(6H,t,2CH$_3$),2.61(4H,t,2CH$_2$),2.92(4H,t,2CH$_2$),3.74 (6H,s,2CH$_3$),4.13(4H,q,2CH$_2$), 6.8–7.2(6H,m,arom–H).
MS(FAB):414(M+).

REFERENCE EXAMPLE 2

Synthesis of 2,2'-diethoxy-5,5'-bis(2-ethoxycarbonylethyl) biphenyl

To an ethanol solution containing 200 mg (0.518 mmol) of 2,2'-dihydroxy-5,5'-bis(2-ethoxycarbonylethyl), 2.18 ml (1.1398 mmol) of a 0.5217N ethanol solution of sodium ethoxide was added and the solvent was evaporated off. The evaporated residue was dried sufficiently and was dissolved in 5 ml of DMF, to which was added 0.211 ml (2.5905 mmol) of ethyl iodide and the mixture was agitated at room temperature for 4 hours. There was further added thereto a DMF suspension containing 28.2 mg (0.4144 mmol) of sodium ethoxide and the resulting mixture was agitated for 1 hour. The solvent of the reaction mixture was evaporated off under reduced pressure and, to the resulting evaporation residue, an amount of chloroform was added. The solution obtained was washed three times with saline solution and was dried over anhydrous sodium sulfate before the solvent was evaporated off. The resulting evaporated residue was subjected to purification by silica gel column chromatography (20 g of WAKO-gel C-200, eluent: toluene and toluene/ethyl acetate of 100/1) to obtain 188.2 mg (0.4258 mmol), 82%) of 2,2'-diethoxy-5,5'-bis(2-ethoxycarbonylethyl) biphenyl as an oily product.

$^1$H—NMR(CDCl$_3$).

δ(ppm): 1.23(6H,t,2CH$_3$),1.25(6H,t,2CH$_3$),2.61(4H,t,2CH$_2$),2.91(4H,t,2CH$_2$),3.97(4H,q,2CH$_2$),4.13(4H,q,2CH$_2$),6.8—7.2(6H,m, arom—H).

MS(FAB):442(M+).

REFERENCE EXAMPLE 3

Synthesis of 2,2'-dipropoxy-5,5'-bis(2-ethoxycarbonylethyl) biphenyl

To an ethanol solution containing 200 mg (0.518 mmol) of 2,2'-dihydroxy-5,5'-bis(2-ethoxycarbonylethyl), 3.78 ml (2.0724 mmol) of a 0.5478N ethanol solution of sodium ethoxide was added and the solvent was evaporated off. The evaporation residue was dried sufficiently and was dissolved in 5 ml of DMF. There was added thereto 0.238 ml (2.591 mmol) of propyl bromide and the mixture was agitated at room temperature for 15 hours, whereupon 0.255 ml (2.591 mmol) of propyl iodide was added. After three hours, a DMF suspension containing 70.5 mg (1.0362 mmol) of sodium ethoxide was added thereto and the resulting mixture was agitated for 4 hours. The solvent of the reaction mixture was evaporated off under reduced pressure and the resulting evaporated solution was washed three times with saline solution and was dried over anhydrous sodium sulfate, before the solvent was evaporated off. The resulting evaporated residue was subjected to purification by silica gel column chromatography (50 g of WAKO-gel C-200, eluent: hexane and hexane/ethyl acetate of 60/1, 40/1, 35/1, 35/1, 30/1 and 25/1) to obtain 129 mg (0.2742 mmol), 53%) of 2,2'-dipropoxy-5,5'-bis(2-ethoxycarbonylethyl) biphenyl as an oily product.

$^1$H—NMR(CDCl$_3$),

δ(ppm): 0.85(6H,t,2CH$_3$),1.23(6H,t,2CH$_3$),1.63(4H,m,2CH$_2$),2.4—2.7 (4H,m,2CH$_2$),2.7—3.0(4H,m,2CH$_3$),3.83(4H,t,2CH$_2$),4.12(4H,q, 2CH$_2$),6.7—7.2(6H,-m,arom—H).

MS(FAB):470(M+).

REFERENCE EXAMPLE 4

Synthesis of 2,2'-dicyclohexylmethoxy-5,5'-bis(2-ethoxycarbonylethyl) biphenyl

To 5 ml of a DMF solution containing 200 mg (0.518 mmol) of 2,2'-dihydroxy-5,5,'-bis(2-ethoxycarbonylethyl) biphenyl and 0.730 ml (5.181 mmol) of cyclohexylmethyl bromide, there were added 286 mg (2.0724 mmol) of anhydrous potassium carbonate and a small amount of copper powder and the resulting mixture was agitated for 24 hours at room temperature. The reaction mixture was filtered by suction through Celite to remove the solid matter, which was washed ethyl acetate. After the solvent in the filtrate was evaporated off under reduced pressure, the residue was dissolved in chloroform. This solution was washed with dilute hydrochloric acid, dilute aqueous sodium bicarbonate, water and saline solution in this sequence and was dried over anhydrous sodium sulfate. The residue obtained after the solvent had been evaporated off was purified by silica gel column chromatography (with 20 g of WAKO-gel C-200, eluent: hexane and hexane/ethyl acetate of 25/1) to obtain 91 mg (0.1574 mmol, 30%) of 2,2'-dicyclohexylmethoxy-5,5'-bis(2-ethoxycarbonylethyl) biphenyl as an oily product.

$^1$H—NMR(CDCl$_3$),

δ(ppm): 0.8–1.8(22H,m,cyclohexyl-H),1.24(6H, t,2CH$_3$),2.58(4H,t,2CH$_2$),2.89 (4H,t,2CH$_2$),3.65(4H,d,2CH$_2$),4.13(4H,q,2CH$_2$),6.8–7.2(6H,m, arom—H).

MS(FAB):578(M+).

EXAMPLE 1

Synthesis of 2,2'-dimethoxy-5,5'-bis(2-carboxyethyl) biphenyl

To 10 ml of an ethanol solution containing 170 mg (0.4111 mmol) of 2,2'-dimethoxy-5,5'-bis(2-ethoxycarbonylethyl) biphenyl obtained in Reference Example 1, 3.3 ml (3.3 mmol) of a 1N solution of sodium hydroxide was added and the mixture was agitated at room temperature for 24 hours. The solvent of the reaction mixture was evaporated off under reduced pressure and, to the resulting evaporation residue, water was added. The solution obtained was acidified by adding 1N hydrochloric acid to a pH of 1–2. The thus-formed precipitate was filtered, washed with water and dried, whereby 145 mg (0.4056 mmol, 99%) of the title compound was obtained as a white solid.

$^1$H-NMR(CDCl$_3$),

δ(ppm): 2.58(4H,t,2CH$_2$),2.87(4H,t,2CH$_2$),3.70(6H,s,2CH$_3$),6.9–7.2 (6H,m,arom—H).

MS(FAB):357(M—H)$^-$.

EXAMPLE 2

Synthesis of 2,2'-diethoxy-5,5'-bis(2-carboxyethyl) biphenyl

To 10 ml of an ethanol solution containing 172 mg (0.3891 mmol) of 2,2'-diethoxy-5,5'-bis(2-ethoxycarbonylethyl) biphenyl obtained in Reference Example 2, 3.1 ml (3.1 mmol) of 1N sodium hydroxide solution was added and the mixture was agitated at room temperature overnight. The solvent of the reaction mixture was evaporated off under reduced pressure and, to the resulting evaporation residue, water was added. The solution obtained was acidified by adding 1N hydrochloric acid to a pH of 1–2. The thus-formed precipitate was filtered, washed with water and dried, whereby 129.6 mg (0.3358 mmol, 86%) of the title compound was obtained as a white solid.

$^1$H-NMR(CDCl$_3$),

δ(ppm): 1.28(6H,t,2CH$_3$),2.59(4H,t,2CH$_2$),2.95(4H,t,2CH$_2$)4.01(4H, q,2CH$_2$),6.8–7.2(6H,-m,arom—H).

MS(FAB):387(M+H)+.

EXAMPLE 3

Synthesis of 2,2'-dipropoxy-5,5'-bis(2-carboxyethyl) biphenyl

To 7 ml of an ethanol solution containing 182.9 mg (0.2742 mmol) of 2,2'-dipropoxy-5,5'-bis(2-ethoxycarbonylethyl) biphenyl obtained in Reference Example 3, 2.2 ml (2.2 mmol) of 1N sodium hydroxide solution was added and the mixture was agitated at room temperature for 2 days. The solvent of the reaction mixture was evaporated off under reduced pressure and, to the resulting evaporation residue, water was added. The solution obtained was acidified by adding 1N hydrochloric acid to a pH of 1-2. The thus-formed precipitate was filtered, washed with water and dried, whereby 108.4 mg (0.2618 mmol, 95%) of the title compound was obtained as a white solid.

$^1$H—NMR(MeOH—d$_4$).

δ(ppm): 0.89(6H,t,2CH$_3$),1.64(4H,m,2CH$_2$),2.4-2.7(4H,m,2CH$_2$),2.7-3.0 (4H,m2CH$_2$),3.86(4H,t,2CH$_2$), 6.8-7.2(6H,m,arom—H).

MS(FAB):413(M-H)$^-$.

EXAMPLE 4

Synthesis of 2,2'-dicyclohexylmethoxy-5,5'-bis(2-carboxyethyl) biphenyl

To 3.6 ml of an ethanol solution containing 86.7 mg (0.1500 mmol) of 2,2'-dicyclohexylmethoxy-5,5'-bis(2-ethoxycarbonylethyl) biphenyl obtained in Reference Example 4, there was added 1.2 ml (1.2 mmol) of 1N sodium hydroxide solution and the mixture was agitated at room temperature. The solvent of the reaction mixture was evaporated off under reduced pressure and, to the resulting evaporated residue, water was added. The solution obtained was acidified adding 1N hydrochloric acid to a pH of 1-2. The thus-formed precipitate was filtrated, washed with water and dried, whereby 75.9 mg (0.1454 mmol, 97%) of the title compound was obtained as a white solid.

$^1$H—NMR(CDCl$_3$).

δ(ppm): 0.8-1.8(22H,m,cyclohexyl-H),2.59 (4H,t,2CH$_2$),2.93(4H,t,2CH$_2$), 3.66(4H,d,2CH$_2$),6.7-7.2(6H,m, arom—H).

MS(FAB):523(M+H)$^+$.

EXAMPLE 5

Synthesis of 2,2'-diethoxy-5,5'-bis(3-methoxycarbonylpropyl) biphenyl

To a methanol solution containing 255 mg (0.6617 mmol) of 2,2'-dihydroxy-5,5'-bis(3-methoxycarbonylpropyl) biphenyl, 4.01 ml (1.9851 mmol) of a 0.4956N methanol solution of sodium methoxide was added and the solvent was evaporated off. The evaporated residue was dried sufficiently and was dissolved in 5 ml of DMF, to which was added 0.270 ml (3.309 mmol) of ethyl iodide and the mixture was agitated at room temperature for 4 hours. There was further added a DMF suspension containing 35.7 mg (0.6617 mmol) of sodium methoxide and the resulting mixture was agitated for 1 hour. The solvent of the reaction mixture was evaporated off under reduced pressure and, to the resulting evaporated residue, chloroform was added. The solution obtained was washed three times with saline solution and was dried over anhydrous sodium sulfate, before the solvent was evaporated off. The resulting evaporated residue was subjected to purification by silica gel column chromatography (20 g of WAKO-gel C-200, eluent: toluene and toluene/ethyl acetate of 100/1 to 80/1) to obtain 191 mg (0.4321 mmol, 65%) of 2,2'-diethoxy-5,5'-bis(3-methoxycarbonylpropyl) biphenyl as an oily product.

$^1$H—NMR(CDCl$_3$).

δ(ppm): 1.25(6H,t,2CH$_3$),1.95(4H,m,2CH$_2$),2.35(4H,t,2CH$_2$)2.61(4H,t,2CH$_2$),3.66(6H,s,2CH$_3$),3.97 (4H,q,2CH$_2$),6.8-7.2(6H,m, arom—H).

MS(FAB:442(M+).

REFERENCE EXAMPLE 6

Synthesis of 2,2'-dipropoxy-5,5'-bis(3-methoxycarbonylpropyl) biphenyl

To a methanol solution containing 143 mg (0.3350 mmol) of 2,2'-dihydroxy-5,5'-bis(3-methoxycarbonylpropyl) biphenyl, 1.35 ml (0.670 mmol) of a 0.4956N methanol solution of sodium methoxide was added and the solvent was evaporated off. The evaporated residue was dried sufficiently and was dissolved in 5 ml of DMF, to which was added to 0.165 ml (1.675 mmol) of propyl iodide and the mixture was agitated at room temperature for 2 hours. There was further added a DMF suspension containing 28.2 mg (0.4144 mmol) of sodium methoxide and the resulting mixture was agitated for 1 hour. The solvent of the reaction mixture was evaporated off under reduced pressure and, to the resulting evaporated residue, chloroform was added. The solution obtained was washed three times with saline solution and was dried over anhydrous sodium sulfate, before the solvent was evaporated off. The resulting evaporated residue was subjected to purification by silica gel column chromatography (20 g of WAKO-gel C-200, eluent: hexane and hexane/ethyl acetate of 16/1) to obtain 94 mg (0.2000 mmol, 60%) of 2,2'-dipropoxy-5,5'-bis(3-methoxycarbonylpropyl) biphenyl as an oily product.

$^1$H—NMR(CDCl$_3$).

δ(ppm): 0.85(6H,t,2CH$_3$),1.3-2.1(8H,m,2CH$_2$,2CH$_2$),2.1-2.4(4H,m,2CH$_2$), 2.4-2.7(4H,m,2CH$_2$),3.65(6H,s, 2CH$_3$),3.83(b 4H,t,2CH$_2$),6.7-7.2 (6h,m,arom—H).

MS(FAB:470(M+).

REFERENCE EXAMPLE 7

Synthesis of 2,2'-dipentyloxy-5,5'-bis(3-methoxycarbonylpropyl) biphenyl

To 10 ml of a DMF solution containing 400 mg (1.0363 mmol) of 2,2'-dihydroxy-5,5'-bis(3-methoxycarbonylpropyl) biphenyl and 0.530 ml (4.145 mmol) of pentyl bromide, there was added 1.14 ml (7.4613 mmol) of DBU and the resulting mixture was agitated for 2 days at room temperature. There was further added 0.795 ml (6.218 mmol) of pentyl bromide and the mixture was further agitated overnight at 65° C., to which was then added 0.1361 ml (1.0363 mmol) of pentyl iodide and the agitation was again continued overnight. The solvent of the reaction mixture was evaporated off under reduced pressure, and, to the resulting evaporated residue, chloroform was added. The obtained solution was washed with dilute hydrochloric acid, water and saline solution in this sequence and was dried over anhydrous sodium sulfate. The residue obtained after the solvent had been evaporated off was purified by silica gel column chromatography (with 40 g of WAKO-gel, C-200, eluent: hexane and hexane/ethyl acetate of 20/1 and 10/1) to obtain 313.2 mg (0.5954 mmol, 57%) of 2,2'-dipentyloxy-5,oxy-5,5'-bis (3-methoxycarbonylpropyl) biphenyl as an oily product.

¹H—NMR(CDCl₃).

δ(ppm): 0.83(6H,t,2CH₃),1.0–1.8(12H,m, 6CH₂),1.8–2.1(4H,m,2CH₂),2.34 (4H,t,2CH₂),2.61(4H,t,2CH₂), 3.66(6H,s,2CH₃),3.86(4H,t, 2CH₂),6.7–7.2(6H,-m,arom-H).

MS(FAB):526 (M+).

REFERENCE EXAMPLE 8

Synthesis of 2,2'-dicyclohexylmethoxy-5,5'-bis(3-methoxycarbonylpropyl) biphenyl To 5 ml of a DMF solution containing 250 mg (0.6477 mmol) of 2,2'-dihydroxy-5,5'-bis(3-methoxycarbonylpropyl) biphenyl and 0.920 ml (6.477 mmol) of cyclohexylmethyl bromide, there was added 360 ml (2.5907 mmol) of anhydrous potassium carbonate and a small amount of copper powder and the resulting mixture was agitated overnight at 100° C. The reaction mixture was filtered by suction through Celite to remove the solid matter, which was washed with ethyl acetate. After the solvent in the filtrate had been evaporated off under reduced pressure, the evaporated residue was dissolved in chloroform. This solution was washed with dilute hydrochloric acid, dilute aqueous sodium bicarbonate, water and saline solution in this sequence and was dried over anhydrous sodium sulfate. The residue obtained after the solvent had been evaporated off was purified by silica gel column chromatography (with 12 g of WAKO-gel C-200, eluent: hexane and hexane/ethyl acetate of 25/1) to obtain 224 mg (0.3877 mmol, 60%) of 2,2'-dicyclohexylmethoxy-5,5'-bis(3-methoxycarbonylpropyl) biphenyl as a white solid.

H—NMR(CDCl₃).

δ(ppm): 0.6–2.2.(26H,m,cyclohexyl-H,2CH₂), 2.34(4H,t,2CH₂),2.60(4H,t, 2CH₂),3.65(4H,d,2CH₂),3.66(6H, s,2CH₃),6.7—7.2(6H,-m,arom—H).

MS(FAB):578(M+).

EXAMPLE 5

Synthesis of 2,2'-diethoxy-5,5'-bis(3-carboxypropyl) biphenyl

To 10 ml of an ethanol solution containing 183.3 mg (0.4147 mmol) of 2,2'-diethoxy-5,5'-bis(3-methoxycarbonylpropyl) biphenyl obtained in Reference Example 5, there was added 3.3 ml (3.3 mmol) of 1N sodium hydroxide solution and the mixture was agitated at room temperature for 24 hours. The solvent of the reaction mixture was evaporated off under reduced pressure and, to the resulting evaporated residue, water was added. The solution obtain was acidified by adding 1N hydrochloric acid to a pH of 1–2. The thus-formed precipitate was filtered, washed with water and dried, whereby 164 mg (0.3966 mmol, 96%) of the title compound was obtained as a white solid.

¹H—NMR(CDCl₃).

δ(ppm): 1.25(6H,t,2CH₃),1.96(4H,m, 2CH₂),2.37(4H,t,2CH₂),2.64 (4H,t,2CH₂),3.97(4H,q,2CH₃), 6.8–7.2(6H,m,arom—H).

MS(FAB):414(M₊).

EXAMPLE 6

Synthesis of 2,2'-dipropoxy-5,5'-bis(3-carboxypropyl) biphenyl

To 5 ml of a methanol solution containing 93.1 mg (0.2106 mmol) of 2,2'-dipropoxy-5,5'-bis(3-methoxycarbonylpropyl) biphenyl obtained in Reference Example 6, 1.7 ml (1.7 mmol) of 1N sodium hydroxide solution was added and the mixture was agitated at room temperature for 2 days. The solvent of the reaction mixture was evaporated off under reduced pressure and, to the resulting evaporated residue, water was added. The solution obtained was washed with ether and was then acidified using 1N hydrochloric acid and then 0.1N hydrochloric acid to a pH of about 3. The thus-formed precipitate was extracted with ethyl acetate and the extract was washed with water and then with saline solution and was then dried over anhydrous sodium sulfate. By evaporating off the solvent, 58.8 mg (0.1330 mmol, 63%) of the title compound was obtained as a white solid.

¹H—NMR(CDCl₃).

δ(ppm): 0.85(6H,t,2CH₃),1.4–2.2(8H,m, 2CH₂,2CH₂),2.37(4H,t,2CH₂), 2.63(4H,t,2CH₂),3.83(4H,t, 2Ch₂),6.7–7.2(6H,-m,arom-H).

MS(FAB):441(M—H⁻).

EXAMPLE 7

Synthesis of 2,2'-dipentyloxy-5,5,'-bis(3-carboxypropyl) biphenyl

To 7 ml of a methanol solution containing 156.6 mg (0.2977 mmol) of 2,2'-dipentyloxy-5,5'-bis(3-methoxycarbonylpropyl) biphenyl obtained in Reference Example 7, 2.4 ml (2.4 mmol) of 1N sodium hydroxide solution was added and the mixture was agitated at room temperature for 24 hours. The solvent of the reaction mixture was evaporated off under reduced pressure and, to the resulting evaporated residue, water was added. The solution obtained was washed with ether and was then acidified using 1N hydrochloric acid and then 0.1N hydrochloric acid to a pH of about 3. The thus-formed precipitate was extracted with ethyl acetate and the extract was washed with water and then with saline solution and was then dried over anhydrous sodium sulfate. By evaporating off the solvent, 69.9 mg (0.1404 mmol, 47%) of the title compound was obtained as a white solid.

¹H—NMR(CDCl₃).

δ(ppm): 0.82(6H,t,2CH₃),1.0–1.8(12H, m,6CH₂),1.8–2.2.(4H,m,2CH₂), 2.36(4H,t,2CH₂),2.63(4H,t, 2CH₂),3.85(4H,t,2CH₂),6.7–7.2 (6H,m,arom—H).

MS(FAB):498(M+).

EXAMPLE 8

Synthesis of 2,2'-dicyclohexylmethoxy-5,5'-bis(3-carboxypropyl) biphenyl

To 4 ml of a methanol solution containing 89.9 mg (0.1555 mmol) of 2,2'-dicyclohexylmethoxy-5,5'-bis(3-methoxycarbonylpropyl) biphenyl obtained in Reference Example 8, 1.3 ml (1.3 mmol) of 1N sodium hydroxide solution was added and the mixture was agitated at room temperature for 4 days. The solvent of the reaction mixture was evaporated off under reduced pressure and, to the resulting evaporated residue, water was added. The solution obtained was washed with ether and was then acidified using 1N hydrochloric acid and then 0.1N hydrochloric acid to a pH of about 3. The thus-formed precipitate was extracted with ethyl acetate and the extract was washed with water and then with saline solution and was then dried over anhydrous sodium sulfate. By evaporating off the solvent, 62.7 mg (0.114 mmol, 73%) of the title compound was obtained as a white solid.

$^1$H—NMR(CDCl$_3$).

δ(ppm): 0.6–2.2(26H,m,2CH$_2$,cyclohexyl-H, 2CH$_2$),2.36(4H,t,2CH$_2$),2.63 (4H,t,2CH$_2$),3.65(4H,d,2CH$_2$), 6.7–7.2(6H,m,arom—H).

MS(FAB):550(M+).

EXAMPLE 9

Production of disodium salt of 2,2'-dimethoxy-5,5'-bis (3-carboxypropyl) biphenyl 376 mg (1 mmol) of a known compound 2,2'-dimethoxy-5,5'-bis (3-carboxypropyl) biphenyl was suspended in 50 ml of distilled water and the compound was dissolved by adding thereto 2 ml of 1N NaOH aq. solution. The solution was concentrated by evaporation under reduced pressure and was subjected to freeze-drying, whereby 427 mg of the title compound was obtained. In the same manner as above, the compounds of formula (I) produced in Examples 2–4 and 6–8 were converted into the corresponding disodium salt.

EXAMPLE 10

Encapsulated Drug

An encapsulated drug product was prepared by encapsulating 200 mg of the mixture of the following composition in each #1 capsule.

| Composition | |
|---|---|
| Disodium salt of 2,2'-dimethoxy-5,5'-bis(3-carboxypropyl) biphenyl | 50 mg |
| Lactose | 50 mg |
| Corn starch | 80 mg |
| Crystallized cellulose | 16 mg |
| Calcium stearate | 4 mg |

EXAMPLE 11

Production of disodium salt of 2,2'-dimethoxy-5,5'-bis (2-carboxyethyl) biphenyl 358 mg (1 mmol) of the compound 2,2'-dimethoxy-5,5'-bis (2-carboxyethyl) biphenyl obtained in Example 1 was suspended in 50 ml of distilled water and the compound was dissolved by adding thereto 2 ml of 1N NaOH aq. solution. The solution was concentrated by evaporation under reduced pressure and was subjected to freeze-drying, whereby 400 mg of the title compound was obtained.

EXAMPLE 12

Encapsulated Drug

An encapsulated drug product was prepared in the same manner as in Example 10 with the exception that the disodium salt of 2,2'-dimethoxy-5,5'-bis(2-carboxyethyl) biphenyl was employed instead of the disodium salt of 2,2'-dimethoxy-5,5'-bis (3-carboxypropyl) biphenyl.

EXAMPLE 13

Production f disodium salt of 2,2'-diethoxy-5,5'-bis (3-carboxypropyl) biphenyl 414 mg (1 mmol) of the compound 2,2'-diethoxy-5,5'-bis (3-carboxypropyl) biphenyl obtained in Example 5 was suspended in 50 ml of distilled water and the compound was dissolved by adding thereto 2 ml of 1N NaOH aq. solution. The solution was concentrated by evaporation under reduced pressure and was subjected to freeze-drying, whereby 455 mg of the title compound was obtained.

EXAMPLE 14

Encapsulated Drug

An encapsulated drug product was prepared in the same manner as in Example 10 with the exception that the disodium salt of 2,2'-diethoxy-5,5'-bis(3-carboxypropyl) biphenyl was employed instead of the disodium salt of 2,2'-dimethoxy-5,5'-bis (3-carboxypropyl) biphenyl.

What is claimed is:

1. An aldose reductase inhibitor, comprising an effective amount of a compound of the formula (I)

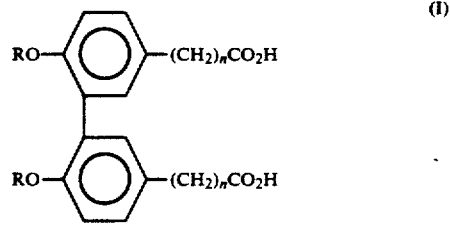

or a pharmaceutically acceptable salt thereof as the effective component, in which R is lower alkyl or cyclohexylmethyl and n is 2 or 3, in admixture with an excipient, said amount being effective to inhibit aldose reductase in a human patient.

2. An aldose reductase inhibitor as in claim 1, wherein 2,2'-dimethoxy-5,5'-bis(3-carboxypropyl) biphenyl or a pharmaceutically acceptable salt thereof is the effective component.

3. An aldose reductase inhibitor as claimed in claim 1, wherein 2,2'-diethoxy-5,5'-bis(3-carboxypropyl) biphenyl or a pharmaceutically acceptable salt thereof is the effective component.

4. An aldose reductase inhibitor as claimed in claim 1, wherein 2,2'-diethoxy-5,5'-bis(3-carboxyethyl) biphenyl or a pharmaceutically acceptable salt thereof is the effective component.

* * * * *